(12) United States Patent
Casey et al.

(10) Patent No.: US 9,354,209 B2
(45) Date of Patent: May 31, 2016

(54) MINIATURE HPLC DEVICE

(75) Inventors: Duncan Robert Casey, London (GB); Joseph John Kaplinsky, London (GB); Ali Salehi-Reyhani, Middlesex (GB)

(73) Assignee: Imperial Innovations Ltd, Greater London (GB)

( * ) Notice: Subject to any disclaimer, the term of this patent is extended or adjusted under 35 U.S.C. 154(b) by 450 days.

(21) Appl. No.: 13/806,233

(22) PCT Filed: Jun. 27, 2011

(86) PCT No.: PCT/GB2011/051217
§ 371 (c)(1),
(2), (4) Date: May 17, 2013

(87) PCT Pub. No.: WO2011/161481
PCT Pub. Date: Dec. 29, 2011

(65) Prior Publication Data
US 2013/0219999 A1    Aug. 29, 2013

(30) Foreign Application Priority Data

Jun. 25, 2010 (GB) .................................. 1010737.3

(51) Int. Cl.
*G01N 30/32*    (2006.01)
*G01N 30/36*    (2006.01)
*F04B 19/00*    (2006.01)
(Continued)

(52) U.S. Cl.
CPC .............. *G01N 30/32* (2013.01); *F04B 19/006* (2013.01); *G01N 30/22* (2013.01); *G01N 30/36* (2013.01); *G01N 30/6095* (2013.01); *G01N 2030/027* (2013.01); *G01N 2030/324* (2013.01); *G01N 2030/326* (2013.01)

(58) Field of Classification Search
CPC .................. G01N 2030/027; G01N 2030/324; G01N 30/32; G01N 30/36
See application file for complete search history.

(56) References Cited

U.S. PATENT DOCUMENTS 4,165,284 A * 8/1979 Guillemin .............. G01N 30/38
                                                          210/198.2
5,408,326 A * 4/1995 Wang ............................ 356/410
(Continued)

FOREIGN PATENT DOCUMENTS

EP    0583003 A1    2/1994
JP    1999287791 A    10/1999
(Continued)

OTHER PUBLICATIONS

Bahnev, et al: Miniaturized Cavity Ring-Down Detection in a Liquid Flow Cell; Analytical Chemistry; 2005, vol. 77, No. 4, pp. 1188-1191.

(Continued)

*Primary Examiner* — Paul West
(74) *Attorney, Agent, or Firm* — Lathrop & Gage LLP; Michael A. Mattoni; Brian C. Trinque

(57) ABSTRACT

A liquid chromatography device comprises one or more liquid reservoirs (3) for a liquid medium, a sample reservoir for a sample to be analyzed and a chromatography column (4) in fluid communication with the liquid reservoir (3) and the sample reservoir (5). The device further comprises a gas reservoir (1) for containing a volume of gas under pressure to force liquid from the liquid reservoir (3) through the chromatography column (4), in use.

24 Claims, 3 Drawing Sheets

(51) Int. Cl.
*G01N 30/22* (2006.01)
*G01N 30/02* (2006.01)
*G01N 30/60* (2006.01)

(56) References Cited

U.S. PATENT DOCUMENTS

| | | | |
|---|---|---|---|
| 6,572,749 | B1 | 6/2003 | Paul et al. |
| 2003/0223913 | A1* | 12/2003 | Karp et al. ............ 422/101 |
| 2004/0124085 | A1 | 7/2004 | Tai et al. |
| 2005/0142662 | A1 | 6/2005 | Bonn |
| 2007/0068872 | A1 | 3/2007 | Gerhardt et al. |
| 2008/0277606 | A1 | 11/2008 | Wang et al. |
| 2009/0150082 | A1 | 6/2009 | Kang et al. |
| 2010/0291691 | A1 | 11/2010 | Sugiyama et al. |

FOREIGN PATENT DOCUMENTS

| | | | |
|---|---|---|---|
| JP | 2003502655 A | | 1/2003 |
| JP | 2005148774 A | * | 6/2005 |
| JP | 2006-515059 A | | 5/2006 |
| JP | 2007163252 A | | 6/2007 |
| JP | 2009-142635 A | | 7/2009 |
| JP | 2009-531665 A | | 9/2009 |
| JP | 2009-532706 A | | 9/2009 |
| WO | 00/78454 A1 | | 12/2000 |
| WO | 2007/111282 A1 | | 10/2007 |
| WO | 2007/112224 A2 | | 10/2007 |
| WO | 2007/118046 A2 | | 10/2007 |

OTHER PUBLICATIONS

Elwenspoek, et al: Towards integrated microliquid handling systems; Journal of Micromechanics & Microengineering; 1994, vol. 4 (4), pp. 227-245.

Khirevich, et al: Large-Scale Simulation of Flow and Transport in Reconstructed HPLC-Microchip Packings; Anal Chem; 2009, vol. 81, pp. 4937-4945.

International Preliminary Report on Patentability, PCT/GB2011/051217, dated Dec. 28, 2012, 8 pages.

* cited by examiner

MINIATURE HPLC DEVICE

RELATED APPLICATIONS

This application is a 35 U.S.C. §371 filing of International Application No. PCT/GB2011/051217 filed Jun. 27, 2011, which claims priority to Great Britain Patent Application No. 1010737.3, filed Jun. 25, 2010. The entire contents of each of the above documents are incorporated herein by reference.

BACKGROUND

This invention relates to a liquid chromatography device.

The field of high pressure liquid chromatography is described in M. Dong, Modern HPLC for Practising Scientists, Wiley, 2006. Briefly, chromatography is used to separate, indentify and quantify compounds from a sample consisting of a mixture of compounds. The sample is dissolved in a fluid mobile phase, which interacts with an immobile, immiscible stationary phase. In high pressure liquid chromatography (HPLC) the stationary phase is usually a column packed with particles, which maybe functionalised. The phases are chosen based on the analyte of interest's affinity towards them, relative to that of the rest of the sample. As the mobile phase moves through the stationary phase, the individual sample components will be retained by the stationary phase to varying degrees and will become separated. The retention time varies depending on the interaction strength with the stationary phase, the composition of solvent used and the flow rate of the mobile phase.

Separation power increases with smaller stationary phase particle size. However, this increases the resistance to flow making the use of high pressures desirable. High pressure liquid chromatography drives the mobile phase through columns containing particles of typical diameters 5-10 micrometers. The first HPLC pumps were capable of 500 psi, with 6000 psi typical today. Ultrahigh pressure liquid chromatography (UPLC) consists of plumbing and pumps capable of performing at 100,000 psi required to drive solvent through columns containing even smaller particles of the order of 1 micrometer diameter.

The detection of separated analytes is possible via one or more techniques, including UV-visible light absorption, fluorescence, light scattering, refractive index analysis or mass spectrometry. These techniques, particularly when used in parallel, allow the identification and absolute quantitation of a very wide range of compounds, and permit a semi-quantitative analysis of even complex, unknown analyte mixtures. Detection signals are referenced to the time of the sample's injection onto the chromatographic column: under identical conditions, a given compound will have a characteristic retention time and it is this which allows its identification. Where the detection technique is destructive the sample cannot be recovered, but in these cases it is often possible to divert a percentage of the eluent flow to a fraction collector if required.

HPLC has found wide applications in the pharmaceutical industry, environmental monitoring, medicine, academia, defence, forensic science, and elsewhere. However, use has been limited by the bulk and expense of HPLC systems. Cubic meter footprints, mains power supplies, large volumes of eluent, weight and mechanical fragility of existing HPLC systems require fixed laboratory installation. The size and the relatively low turnover of such systems have conspired to make the units extremely expensive both in terms of initial expenditure and then in terms of maintenance and servicing. Typical systems cost tens of thousands of pounds, putting them beyond the reach of all but large, well-established companies and research institutions. Furthermore, the small diameter of HPLC tubing coupled with the crude form of many of the samples analysed via this technique mean that blockages are frequent. The pressure build-up following such an event can cause significant damage to an HPLC, and even if such damage is avoided extended machine down-time is unavoidable.

The component most resistant to miniaturisation has been the pump.

For example, it is stated that a "reason for the limited interest in HPLC-like separations on chip appears to be the complexity of the plumbing since an external pump typical of standard HPLC instrumentation has to be included. The role of the chip then degrades to a capillary-like column and the advantages attributed to microfluidic devices vanish." (Svec and Stachowiak, in Handbook of capillary and microchip electrophoresis and associated microtechniques, ed James P. Landes, CRC Press, 2008, p 1299).

The implementation of integrated microscale HPLC "has proven to be tedious, mostly for reasons related to pressure: the difficulty of generating high pressure with on-chip integrated pumps as well as of fabricating high-pressure rating microchips. Consequently, on-chip liquid chromatography is underdeveloped, not only compared to other chip-based analytical techniques but also in view of the importance of HPLC as an analytical technique." (Khirevich et al. Anal. Chem., 2009, 81 (12), pp 4937-4945).

U.S. Pat. No. 6,572,749 notes that the problem of pumping for micro-HPLC is unsolved and teaches the use of electro-osmotic pumping. However, it only achieves 2500 psi, is dependent on lengthy columns and, in common with other electro-osmotic pumps, that there is interaction between the packing and the electro-osmotic flow.

Although the technology exists to allow the miniaturisation of stages such as detection, while complex pump systems ensure the footprint of the units remains so high there is little incentive to do so.

The invention described herein, at least in its presently preferred embodiments, addresses these and related needs.

BRIEF SUMMARY OF THE DISCLOSURE

In accordance with the present invention there is provided a liquid chromatography device comprising one or more liquid reservoirs for a liquid medium, a sample reservoir for a sample to be analysed and a chromatography column in fluid communication with the liquid reservoir and the sample reservoir. The device further comprises a gas reservoir for containing a volume of gas under pressure to force liquid from the liquid reservoir through the chromatography column, in use.

Thus, in accordance with the invention as gas reservoir is used to propel the liquid through the chromatography column, so that a pump is unnecessary.

The device may comprise a valve to control release of the gas from the gas reservoir. In one embodiment, the gas reservoir may be sealed by a rupturable closure, which is ruptured to release the gas, in use. In this way, the gas reservoir may be single-use. The gas reservoir and the liquid reservoir may be separated by a deformable membrane. In this way, the gas can propel liquid through the chromatography column without the gas contacting the liquid.

The chromatography column may be provided in a channel having a width in the range of 1 to 5,000 micrometers, preferably 20 to 200 micrometers. The chromatography column may be provided in a channel having a length in the range of 1 to 100 centimeters, preferably 2 to 20 centimeters.

The device may comprise one or more detectors downstream of the chromatography column. The detector(s) may be optical, electrical, radiological, for example. The detector(s) may be arranged about a fluid channel in fluid communication with the chromatography column. The detection path of the detector(s) may be transverse, for example perpendicular, to the flow path of the fluid. Alternatively, the detection path of the detector(s) may be substantially parallel to the flow path of the fluid.

The optical detector(s) may comprise, for example, one or more photodiodes. The optical detector may comprise one or more LEDs as a light source.

The optical detector may comprise opposed reflective surfaces on opposite sides of the fluid channel, the opposed reflective surfaces defining an optical cavity. The reflective surfaces may be provided as a layer on the walls of the fluid channel. The optical detector may comprise multiple light sources.

The device may comprise a fluid disposal reservoir in fluid communication with the chromatography column for retaining fluid that has passed through the column for subsequent disposal.

The device may be battery powered. Alternatively or in addition, the device may be powered via a USB connection.

The device may be disposable and/or consumable, in whole or in part.

The device may be connectable to a handheld data processing device, such as a smartphone, for processing the results of the chromatography.

BRIEF DESCRIPTION OF THE DRAWINGS

Embodiments of the invention are further described hereinafter with reference to the accompanying drawings, in which.

DETAILED DESCRIPTION

Embodiments of the present invention relate to miniaturising the format of high pressure liquid chromatography by use of a gas reservoir for pumping the mobile phase, to a point where the device is fully portable and/or disposable. An embodiment of the invention is a miniaturised HPLC device in which pressure to move the mobile phase is provided by release of gas from a pre-pressurised reservoir, dispensing with the need for a conventional pump integrated into the device. The device may be portable and disposable.

Figure 1:
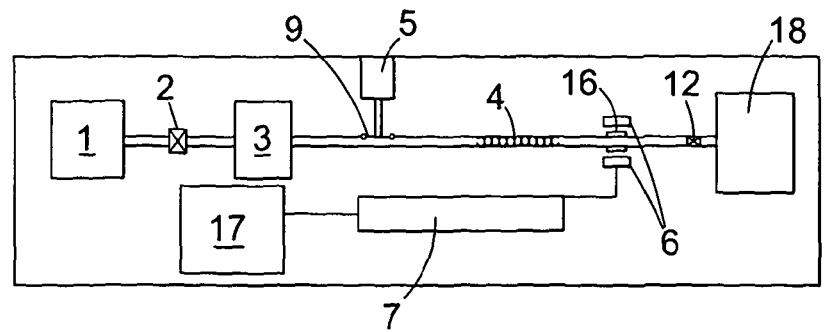
FIG. 1 is a schematic representation of an HPLC device according to an embodiment of the invention.

As exemplified in FIG. 1, an embodiment of the invention comprises a pump system consisting of a gas reservoir 1 containing pre-pressurised gas at a pressure suitable for running HPLC and a (solenoid) valve 2 which when opened provides pressure to drive the mobile phase through the HPLC column. The device further comprises a mobile phase reservoir 3 and capillary column 4 packed with a solid phase suitable for HPLC separation. A sample introduction system comprises a sample reservoir 5. A detection system 6 is provided that is capable of detecting analyte fractions separated by the HPLC stage. In the example shown the detection system 6 comprises a light emitting diode (LED) and a photodiode. A microelectronic controller 7 is provided that is capable of controlling the device and processing data from the detection system 6.

As the instrument is intended to be disposable, it does not have the same longevity requirements that make existing models so large and cumbersome. In one embodiment the device is single use. Alternatively the device could be designed for hundreds or thousands of runs.

The pump gas reservoir 1 may be a steel-walled cylinder. The valve 2 is preferably electronically controlled, such as a solenoid valve. However, if the device is intended as single use the gas may be released via a mechanism which breaks a perforable seal on the gas reservoir.

The small column volume means that a gas stored under pressure has limited space to expand, driving solvent before it at a rate that is predictable and reproducible assuming there are no major changes in temperature during a run. The pressure of the gas does not alter significantly during the working life of the unit, meaning that repeated analyses produce identical conditions within the device, and thus identical retention times.

A wide range of gases may be used. For example, nitrogen is cheap and inert. The gas in the gas reservoir and the mobile-phase in the mobile-phase reservoir may be separated by a deformable membrane.

The gas reservoir 1 should be large enough that the fall in pressure in moving mobile phase through the column volume is small. For a gas that behaves approximately as an ideal gas the fractional drop in pressure is equal to the fractional increase in volume. Therefore a reservoir 1 of 10 cubic centimeters moving mobile phase through a 10 microliter column volume will experience a pressure drop of 0.1%. This could conveniently be contained in a spherical reservoir with an inner diameter of 27 millimeters.

The device can function with larger pressure drops, such as 1% or 10%. Because the drop is always reproducible it can be compensated for when identifying peaks at a data processing stage.

Larger reservoirs may be used for larger column volumes, for greater precision or to make multiple separations through the same column volume. A handheld device could easily contain a 100 cubic centimeter reservoir.

The pressure provided by the pumping system is subject to variation with temperature. For an ideal gas a change in temperature of 3 Kelvin is expected to change the pressure by about 1%. The device may optionally incorporate a thermometer so that temperature variation can be corrected for at a data processing stage. The device may also optionally include mechanisms for heating or cooling, such as ohmic heating or thermoelectric cooling.

The working column volume of the device is typically of the range of 0.1-10 microliters, meaning that a mobile phase reservoir of 1-5 ml permits hundreds of column volumes of chromatography. If the device comprises more than one mobile phase reservoir, eluents may be mixed via the activity of valves permitting the creation of gradient elution profiles; devices with just one reservoir are restricted to isocratic analyses.

In an embodiment whereby the device comprises a single reservoir 3, an isocratic analysis will involve the column being first wetted with solvent followed by elution of a sample plug through the solid phase.

Figure 2:
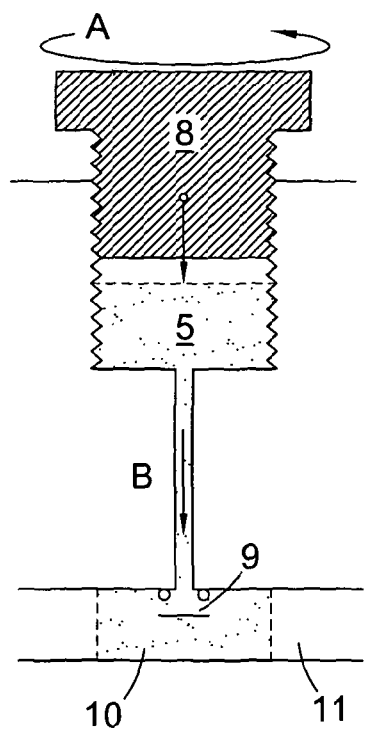
FIG. 2 is a schematic representation of the sample loading configuration of the embodiment of FIG. 1.

As exemplified in FIG. 2, the sample is loaded into the device via a dedicated sample line. In the exemplified embodiment the sample reservoir 5 is threaded so that once filled a screw fixing 8 may be turned (see arrow A) to displace sample into the device (see arrow B). The sample volume may be precisely controlled and depends on the thread pitch and degree by which the screw fixing 8 is rotated. A check valve 9 installed at the union of the sample line and column ensures any sample loaded into the device is not returned. The check valve 9 is opened during sample loading. In FIG. 2, the sample plug 10 and solvent 11 are shown.

An electronically actuated valve 2 is installed between the gas reservoir 1 and the mobile phase reservoir 3 which controls the flow of the mobile phase through the column. The valve 2 is switched to enable the correct sequence of wetting, loading and elution of the column. In the exemplified embodiment the valve is a hydraulic solenoid controlled by the on-board microelectronics 7 which is capable of withstanding pressures typical of HPLC.

Alternatively, the sample may be introduced through a sample introduction loop switched into the column path, as in conventional HPLC.

The separation stage of the device comprise a capillary 4 or micro-machined channel within a substrate with an inner diameter in the range of 1-5000 micrometers and a length of 1-100 cm, filled with a solid phase bed of either particulate material such as silica, with a polymer structure, or with an inorganic monolith structure. This packing may be functionalised to give specific chemical or structural selectivity, or it may contain pores of controlled size in order to separate mixtures via diffusive processes as in size exclusion chromatography. In general, any of the solid phases used in HPLC may be used.

In a preferred embodiment the column is a packed fused-silica capillary with inner diameter in the range 20-200 micrometers, length in the range 2-20 cm and with optical transparency suitable for use with UV absorption measurements. The packing of capillary and compatible connections have been documented elsewhere (E. Rapp & E. Bayer, J. Chromatography A, 2000 (887) pp 367-378).

Figure 3:
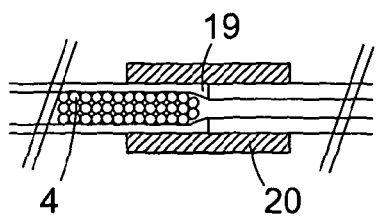
FIG. 3 is a schematic representation of a connection of the embodiment of FIG. 1.

FIG. 3 shows connecting tubing and capillaries. The join must be able to withstand typical HPLC pressures. An internal taper 19 and a shrink-tube connector 20 are provided.

In order to prevent dissolved gas effervescing from the eluent stream in the device in between the column and the detection stage 6, a back pressure regulator 12 is fitted to the end of the solvent path. This is configured to supply a back-pressure equivalent or greater than the pressure exerted by the separation phase, meaning that de-gassing of the eluent stream is prevented until it has left the device.

The detection system may be optical, electrical or radiological, the choice of which will be dependent on the intended application of the device. In the exemplified embodiment the detection system is based on optical detection. The optical detection system 6 comprises one or an array of light emitting diodes (LEDs) 13 which form a source and one or an array of photodiodes 14 operating in the ultraviolet, visible or infrared wavelength regions, which form a detector. In the exemplified embodiment the mode of detection is UV-VIS absorption spectroscopy. Light is passed through the sample and a signal is detected by a photodiode 14. The strength of the signal is inversely proportional to the amount of absorber in the detection path. The amount absorbed is dependent upon the Beer-Lambert law:

$$A(\lambda) = \in(\lambda) c l,$$

where $A(\lambda)$ is the absorbance at a particular wavelength, $\in(\lambda)$ is the molar absorption coefficient of the absorber at the given wavelength, c is the concentration of the absorber and l is the total path length which the light passes through the absorber. The absorbance is characteristic for any given compound at any given wavelength.

Figure 4A:
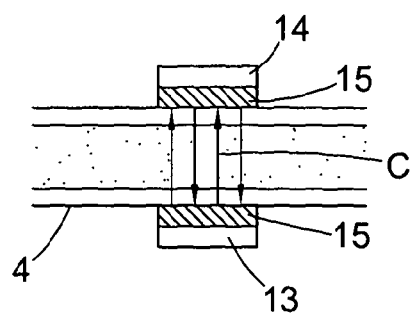
FIGS. 4a and 4b illustrate the CRDS detection system of an embodiment of the invention.
Figure 4B:
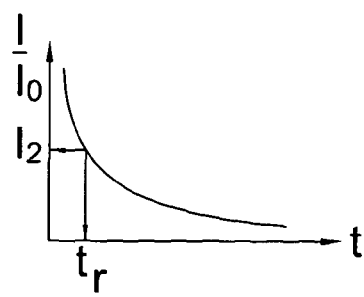

The short path length available for absorption makes desirable systems to increase sensitivity by enhancing absorption. Absorption may be enhanced using a multi-pass arrangement and forms the basic principle of cavity ring-down spectroscopy (CRDS, described in detail in L. Van der Sneppen et al, Annu. Rev. Anal. Chem 2009 2 pp 13-35). The CRDS setup typically consists of a light source used to illuminate an optical cavity, which may simply be composed of two highly reflective mirrors. As shown in FIG. 4, highly reflective mirrors or coatings 15 are provided on either side of the detection path so that multiple light paths through the absorber are created as indicated by arrow C. Intensity builds up within the cavity until the light source is switched off and the exponential decay of light leaking from the cavity is measured (see FIG. 4a). The ringdown time $t_r$ is the time taken for light to decay to lie of its initial intensity and decreases by a degree determined by the amount of absorber present in the cavity.

Several CRDS modes exist such as evanescent wave-CRDS, continuous wave-CRDS and are all suitable as part of the detection apparatus. The preferred embodiment is CW-CRDS since low cost LEDs may be used instead of a laser system.

The optical cavity 16 may be formed by coating the capillary or channel with a suitable dielectric. This makes the detection apparatus amenable to mass production.

In HPLC, absorption spectroscopy is typically conducted by directing the incident radiation perpendicular to the flow of the absorbing species. To increase sensitivity while employing a single-pass arrangement the incident radiation may be directed in a direction parallel to the flow of the absorbing species. In this case, the detection apparatus is arranged relative to the flow line such that it would afford the coupling in and out of radiation that would be absorbed along the flow path by the absorbing species. The distance between the locations along the fluid line after the separation column where radiation is coupled in and out may be greater than the thickness (diameter if circular) of the fluid line thus increasing the distance over which radiation may be absorbed and enhancing sensitivity.

The on-board electronics may be driven by a simple microcontroller 7.

In one embodiment the HPLC unit may be connected to a data processing device such as a smart phone or a personal computer. The connection may be wired or wireless for example by a USB interface 21. The device may process data uploaded from the HPLC unit, providing access to chromatograms, identification and quantification of analytes. The device may also be capable of transmitting data via a telecommunication network for remote processing.

The connection to the data processing device may also be used to deliver power to the HPLC unit, for example through a USB cable. The power requirements of the HPLC unit are low enough to have a small impact on the battery life of a portable PC or smartphone. By making use of a battery and processing power in an attached data processing device the cost and size of the HPLC unit may be further reduced. The power module 17, which may be a battery or USB connection, for example, is shown in FIG. 1.

This data processing device may also be capable of transmitting data via a telecommunication network for remote processing. Such data processing may be also performed locally on a sufficiently computationally powerful device such as a smartphone.

Another embodiment of the device enables entirely standalone operation, for use as a field diagnostic test. In this case, power may be supplied either by a battery or via a small solar cell, whereas the data readout may be visualised using an integrated LCD or LED display. By minimising the use of moving parts and by using low power, solid-state components wherever possible, the power consumption of the device is so small as to allow even fully wire-free operations in regions or environments where mains power is unavailable. Data gathered in this embodiment of the device may be stored on a removable memory unit such as a flash memory card for later analysis.

Once the sample has been analysed by the device it may be passed into a waste collection reservoir 18. This allows the sample to be catalogued for further analysis or storage. The reservoir 18 may hold samples requiring disposal in accordance with federal, state and local environmental control regulations.

Figure 5:
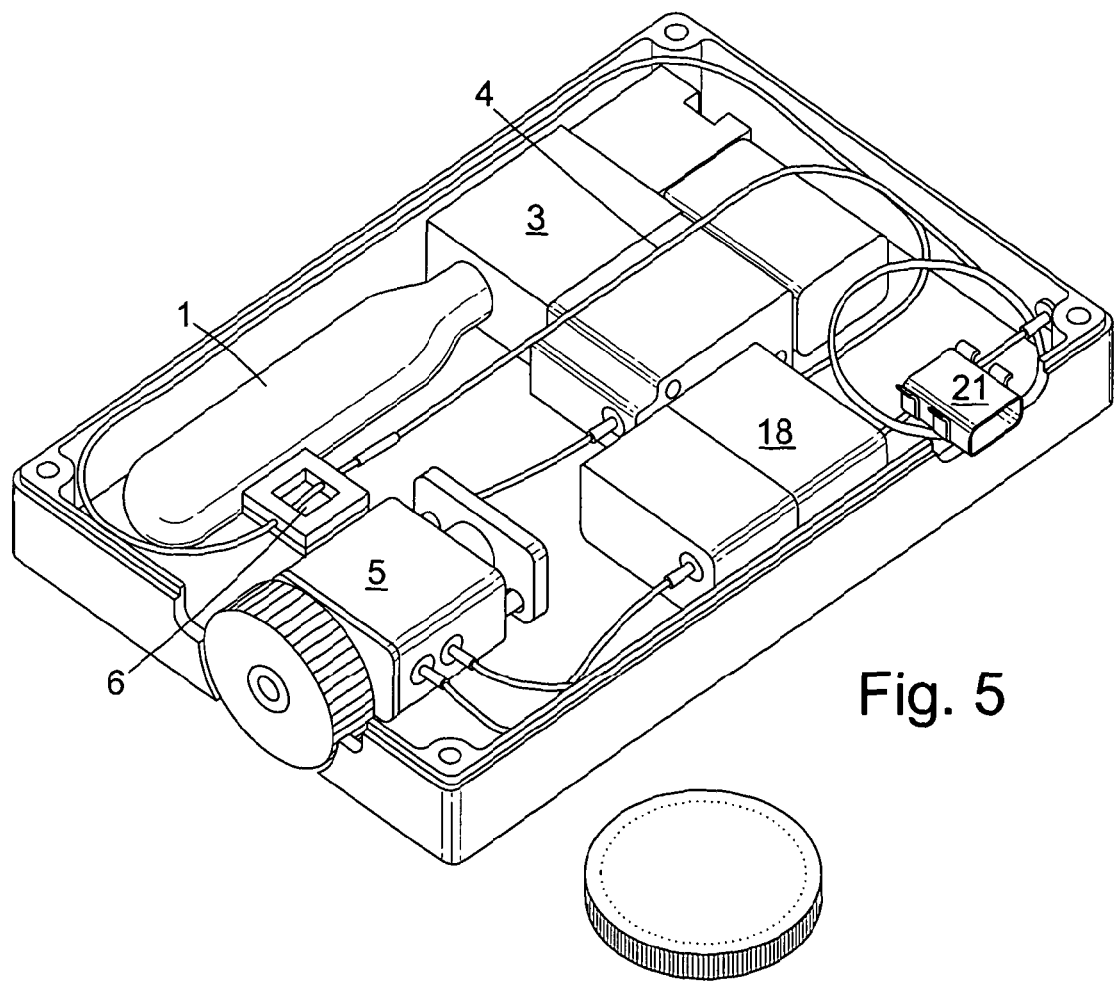
FIG. 5 illustrates and embodiment of the invention.

FIG. 5 shows the physical arrangement of the components in the device using the reference numerals of the preceding Figures. A British one pound coin is shown for scale.

Figure 6:
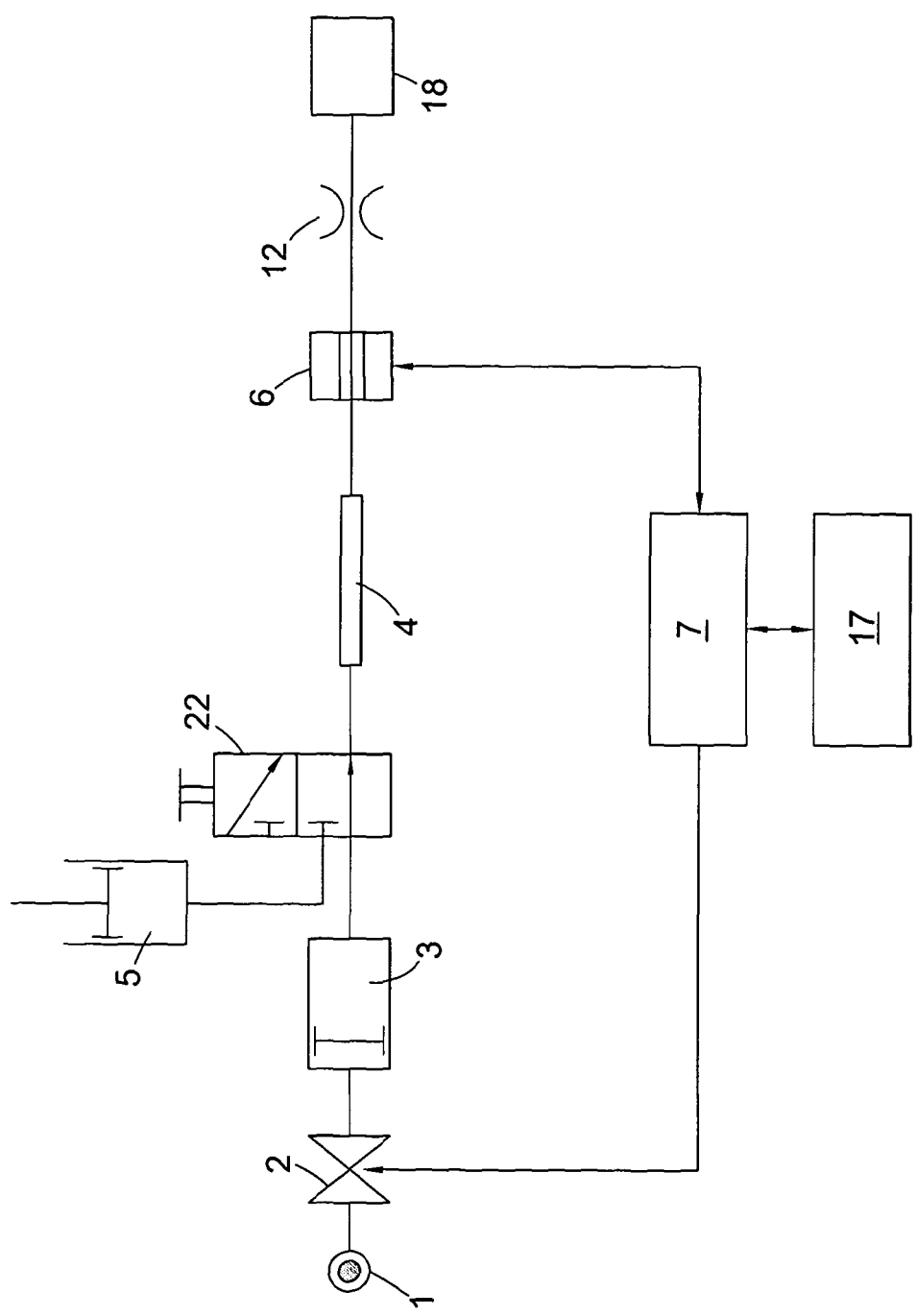
FIG. 6 is a schematic representation of an HPLC device according to an alternative embodiment of the invention.

FIG. 6 is a further schematic representation of an embodiment of the invention in which the same reference numerals as in the preceding Figures are used for corresponding components. In this embodiment, a manual directional control valve 22 having three ports and two positions is provided for sample injection.

In summary, a liquid chromatography device comprises one or more liquid reservoirs 3 for a liquid medium, a sample reservoir 5 for a sample to be analysed and a chromatography column 4 in fluid communication with the liquid reservoir 3 and the sample reservoir 5. The device further comprises a gas reservoir 1 for containing a volume of gas under pressure to force liquid from the liquid reservoir 3 through the chromatography column 4, in use.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The invention claimed is:

1. A liquid chromatography device comprising:
   one or more liquid reservoirs for a liquid medium,
   a sample reservoir for a sample to be analysed,
   a chromatography column in fluid communication with the liquid reservoir and the sample reservoir,
   a pre-pressurized gas reservoir for containing a volume of gas under an initial pressure, wherein a fraction of the volume of gas released from the gas reservoir at the initial pressure is sufficient to force a first portion of liquid from the liquid reservoir through the chromatography column, in use, and
   a housing containing the one or more liquid reservoirs, the sample reservoir, the chromatography column, and the gas reservoir,
   wherein the volume of the gas reservoir is sized such that the volume of gas remaining within the gas reservoir, after release of the fractional volume of gas, is under a residual pressure sufficient to force a second portion of liquid from the liquid reservoir through the chromatography column.

2. A liquid chromatography device as claimed in claim 1, wherein the chromatography column is provided in a channel having a width in the range of 1 to 5,000 micrometers.

3. A liquid chromatography device as claimed in claim 2, wherein the width of the chromatography column is within the range of 20 to 5,000 micrometers.

4. A liquid chromatography device as claimed in claim 1, wherein a length of the chromatography column is in the range of 1 to 100 centimeters.

5. A liquid chromatography device as claimed in claim 4, wherein the length of the chromatography column is within the range of 2 to 100 centimeters.

6. A liquid chromatography device as claimed in claim 1 further comprising one or more optical detectors downstream of the chromatography column and arranged about a fluid channel in fluid communication with the chromatography column.

7. A liquid chromatography device as claimed in claim 6, wherein the optical detector comprises at least one LED as a light source.

8. A liquid chromatography device as claimed in claim 6, wherein the optical detector comprises opposed reflective surfaces on opposite sides of the fluid channel, the opposed reflective surfaces defining an optical cavity.

9. A liquid chromatography device as claimed in claim 8, wherein the reflective surfaces are provided as a layer on the walls of the fluid channel.

10. A liquid chromatography device as claimed in claim 6, wherein the optical detector comprises multiple light sources.

11. A liquid chromatography device as claimed in claim 1 further comprising a fluid disposal reservoir in fluid communication with the chromatography column for retaining fluid that has passed through the column for subsequent disposal.

12. A liquid chromatography device as claimed in claim 1, wherein the device is battery powered.

13. A liquid chromatography device as claimed in claim 1, wherein the device is disposable.

14. A liquid chromatography device as claimed in claim 1, wherein the device is connectable to a handheld data processing device for processing the results of the chromatography.

15. A liquid chromatography device as claimed in claim 1, wherein the device does not include a pump external to the housing to force liquid from the liquid reservoir through the chromatography column.

16. A liquid chromatography device as claimed in claim 1, wherein the volume of the gas reservoir is of sufficient size such that a fractional drop in pressure within the gas reservoir resulting from release of the fractional volume of gas to move the first portion of liquid through the chromatography column is equal to a fractional increase in volume in the gas reservoir.

17. A liquid chromatography device as claimed in claim 1, wherein the fractional drop in pressure is less than or equal to 10%.

18. A liquid chromatography device as claimed in claim 1, wherein the volume of the gas reservoir is of sufficient size such that a pressure exerted by the volume of gas contained within the gas reservoir is substantially constant when moving the liquid medium through the chromatography column.

19. A liquid chromatography device as claimed in claim 1, wherein the volume of the gas reservoir is selected within the range between 1 to 100 cubic centimeters.

20. A liquid chromatography device as claimed in claim 1, further comprising a thermometer for measuring a temperature of the device.

21. A liquid chromatography device as claimed in claim 1, further comprising a mechanism for heating or cooling the device.

22. A liquid chromatography device as claimed in claim 1, further comprising a valve to control release of gas from the gas reservoir.

23. A liquid chromatography device as claimed in claim 1 or 22, wherein the gas reservoir and the liquid reservoir are separated by a deformable membrane.

24. A liquid chromatography device as claimed in claim 1 or 22, wherein the gas reservoir and the liquid reservoir are separated by a rupturable membrane.

\* \* \* \* \*